(12) United States Patent
Dubey et al.

(10) Patent No.: US 10,111,921 B2
(45) Date of Patent: Oct. 30, 2018

(54) REGULATION OF BRAIN BIOGENIC AMINES ASSOCIATED WITH DEPRESSION BY A FORMULATION FROM BOTANICAL SOURCE

(71) Applicants: Harinder Singh Gill, Bathinda (IN); Govind Prasad Dubey, Varanasi (IN)

(72) Inventors: Rajesh Dubey, Brookline, MA (US); Shipra Dubey, Brookline, MA (US); Govind Prasad Dubey, Varanasi (IN); Aruna Agrawal, Varanasi (IN); Gur Prit Inder Singh, Bathinda (IN); Rashi Bajpai, Kharadi (IN)

(73) Assignees: GoVind Prasad Dubey, Uttar Pradesh (IN); Harinder Singh Gill, Punjab (IN)

( * ) Notice: Subject to any disclaimer, the term of this patent is extended or adjusted under 35 U.S.C. 154(b) by 0 days.

(21) Appl. No.: 15/695,564

(22) Filed: Sep. 5, 2017

(65) Prior Publication Data
US 2018/0055901 A1 Mar. 1, 2018

Related U.S. Application Data

(63) Continuation of application No. 14/660,385, filed on Mar. 17, 2015, now abandoned.

(30) Foreign Application Priority Data

Dec. 6, 2014 (IN) ............................ 6161/CHE/2014

(51) Int. Cl.
*A61K 36/00* (2006.01)
*A61K 36/63* (2006.01)
*A61K 45/06* (2006.01)
*A61K 36/185* (2006.01)
*A61K 36/53* (2006.01)

(52) U.S. Cl.
CPC ............ *A61K 36/63* (2013.01); *A61K 36/185* (2013.01); *A61K 36/53* (2013.01); *A61K 45/06* (2013.01)

(58) Field of Classification Search
CPC ...................................................... A61K 36/00
USPC ........................................................ 424/725
See application file for complete search history.

(56) References Cited

FOREIGN PATENT DOCUMENTS

WO WO2007/042902 A2 4/2007

OTHER PUBLICATIONS

Olsen et al. The internal and external validity of the Major Depression Inventory in measuring severity of depressive states. Psychological Medicine 2003, pp. 351-356, vol. 33.

*Primary Examiner* — Michael V Meller
(74) *Attorney, Agent, or Firm* — The Webb Law Firm

(57) ABSTRACT

Provided herein are anti depressant and anxiolytic herbal formulations including: 225-450 mg of *Nyctanthes arbortristis*, 250-550 mg *Ocimum tenuiflorum*, 200-450 mg *Hippophae salicifolia*, and optionally additives selected from minerals, vitamins, salt, filler and binder. Also provided are methods of making such formulations and methods of using such formulations for treating or improving brain function.

14 Claims, 1 Drawing Sheet

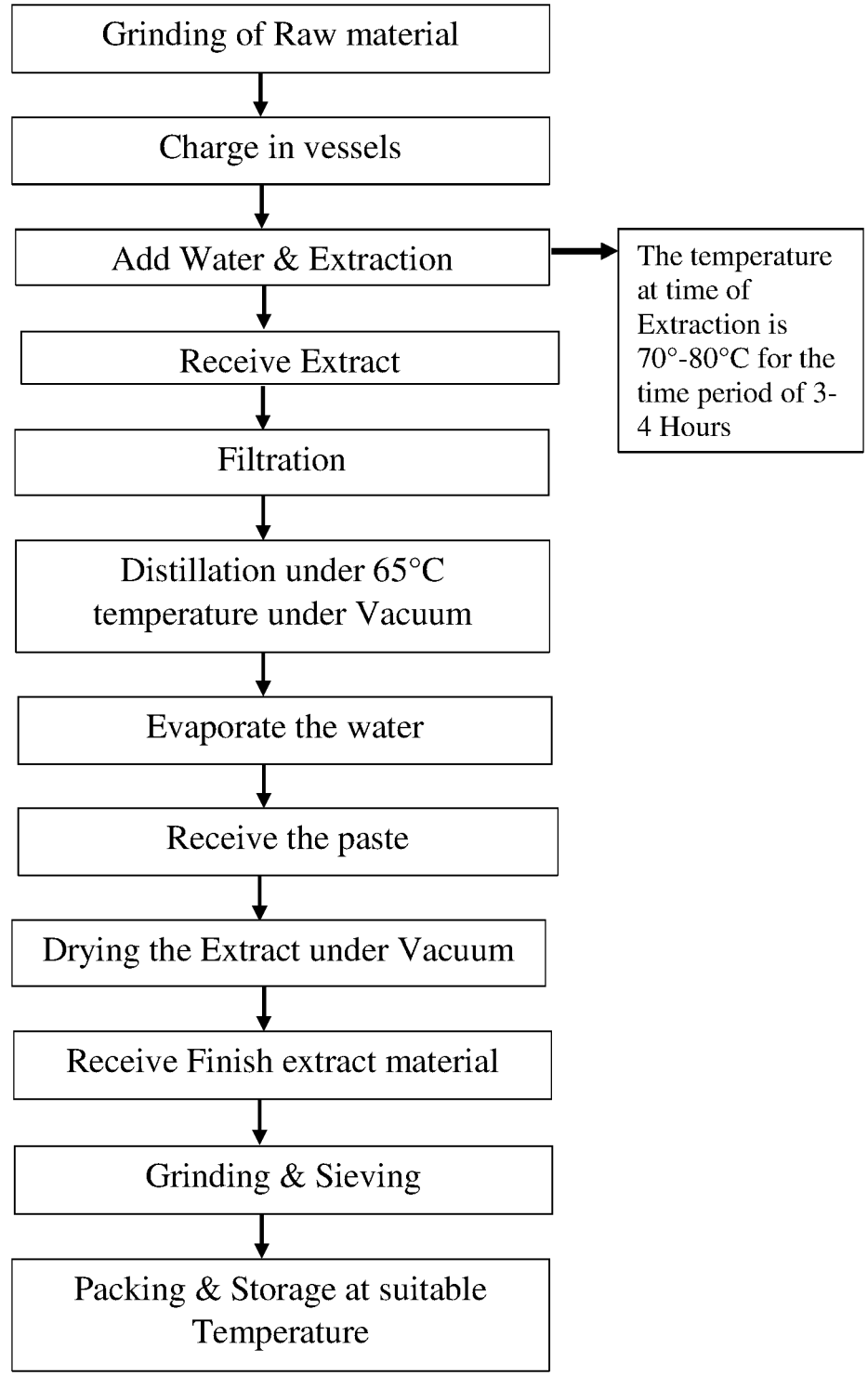

REGULATION OF BRAIN BIOGENIC AMINES ASSOCIATED WITH DEPRESSION BY A FORMULATION FROM BOTANICAL SOURCE

CROSS REFERENCE TO RELATED APPLICATIONS

This application is a continuation application of U.S. patent application Ser. No. 14/660,385, filed Mar. 17, 2015, entitled "Regulation of Brain Biogenic Amines Associated with Depression by a Formulation from Botanical Source" which claims priority to Indian Patent Application No. 6161/CHE/2014, filed on Dec. 6, 2014, which are hereby incorporated by reference in their entirety.

FIELD OF INVENTION

Present invention relates to the development of a plant based formulation beneficial in the management of mild to moderate depression. This preparation may be further advantageous if used for the management of sleep disorders, behavioral abnormalities like psychotic and neurotic behavior, cognitive dysfunction, etc. The pharmacological activity of test formulation can be evaluated on neurotransmitter biochemistry including biogenic amine like dopamine, GABA, glutamate, 5-HT serotonin and also anxiety and depression scores as these bio-markers are significantly involved with depressive behavior. Melatonin is one of the most important targeted markers involved with depression and having a role in regulation of sleep. The activity of test formulation can be assessed on melatonin receptors distributed in different part of the brain and the drug can activate either the wake related neuronal down stream pathways or promote sleep related pathways.

Background of Study:

Depression is a significant contributor to the major disease burden affecting almost all the communities worldwide. Recently the incidence is reported to be significantly high, mentioning that 350 million people are affected from depression. The World Mental Health conducted a survey and reported that 1 in 20 people is having an episode of depression. Depressive disorders often start at a young age affecting their quality of life. Moreover, depression often comes with symptoms of anxiety. These complaints can become chronic or recurrent and lead to substantial impairment of an individual's ability to take care of him- or herself in day to day life. The worst part of depressive disorder is the development of suicidal tendency which is reported around 9000 suicidal deaths every day.

The clinical symptoms associated with depression are depressed mood, loss of interest and enjoyment and increased early fatigue. Based on symptoms a depressive episode can be categorized as mild, moderate or severe. An individual with mild depressive episode will have some difficulty in continuing with ordinary work and social activities.

The burden of depression is 50 percent higher for females than males (WHO 2008). Maternal depression may be a major risk factor for poor growth in young children. Depression affects not only this generation but also the next.

Disturbance of the sleep/wake cycle is one of the DSM-IV diagnostic criteria for depression and people with major depression commonly experience changes in sleep wake cycle regulation that are seen as an abnormal total sleep duration, poor sleep efficiency overwhelming rapid eye movement (REM) sleep and early morning awakening. A good number of depressive patients show regular changes in the intensity of depressive mood during the day, with parallel changes in anxiety symptoms that frequently accompany depression. Further, in patients with unipolar and bipolar depression, evidence has been provided for a phase advance of the temperature—REM sleep cycle in relation to the rest/activity cycle, and melatonin secretion studies of patients with depressive disorders.

A number of studies have investigated variants of genes that control the circadian system for their association with mood disorder and circadian related polymorphism in depressive disorders.

Recently attention has been paid towards the investigations of patho-physiology involved with affective disorders and their efficient treatment. The drug being used for the management of depression is based on modulation of nor-adrenergic and serotonergic neurotransmitters mainly known as nor-adrenergic reuptake inhibitors as well as MAO inhibitors. A significant decrease in nor-adrenergic and serotonergic neuro-hormones are reported which are regulated through intervention of anti-depressant agents. As reported over activation of glutamate and the decreased activity of GABA is responsible for mood disorders. However, a long term treatment can only produce desired results and moreover in most of the depression patient this treatment is not much effective. Further, the workers have reported that the anti-depressant drugs influence excitatory and inhibitory neurotransmitter which contributes to their efficacy. Thus, this type of activity may have better anti-depressant effect.

The treatment option consists of basic psychosocial support combined with anti-depressant medication along with psychotherapy such as cognitive behavior therapy, interpersonal psychotherapy or problem solving treatment. Anti-depressant medications and brief psychotherapy programs are effective. Anti-depressants can be a very effective form of treatment for moderate to severe depression but are not the first line treatment.

It is postulated that depression is the outcome of deficiency of various amines which serve as neuro-transmitters in the brain. The tricyclic agents are anti-cholinergic effects, may cause postural hypertension and cardio-toxicity. Currently available drugs are fluoxetine that are selective inhibitors of 5-HT re-uptake, MAO inhibitors which enhances the availability of neuro-transmitters at synaptic cleft by inhibiting metabolism of nor-epinephrine and 5-HT, and are less effective than tricyclic or less effective in severe depression. Further, studies are there showing that MAO inhibitors are more useful when depression is associated with anxiety and phobic reactions. A number of studies have indicated an increased level of platelet MAO in large series of depressed patients. It is also pointed out that the administration of tyrosine in the body increases the rates of brain neuron synthesis of both dopamine and nor-epinephrine. A decreased symptoms of depression after tyrosine administration is reported which in turn indicates the decrease in the level of tyrosine and increased MAO activity.

Anti-depressant drugs act through neurotransmitters in circulation as well as brain tissues. It has been pointed out that catecholamine and serotonin metabolism is impaired during mental depression. Any synthetic medication beneficial in the management of psychiatric illness produces incontinence, discomfort, pathologic changes and some times danger to the patients.

However, the mechanism of action of anti-depressant drugs must be considered in terms of its activity on melatonin receptors ($MT_1$ & $MT_2$ receptors), distributed in the brain, present in suprachiasmatic nucleus (SCN) of prefrontal cortex, cerebellar cortex, hippocampus, basal ganglia, substantia nigra, ventral segmental area, nucleus accumbens, etc. Another possible mode of action of an anti-depressant drug is $MT_1$ mediated effects in SCN favor sleep initiation via the hypothalamic sleep switch, a mechanism characterized by typical on-off responses. The mechanism involved with this kind of sleep pattern is mainly characterized by typical on-off responses. The mode of action activates either wake-related neuronal downstream pathways or promotes sleep-related pathways. Apart from sleep promotion, melatonin receptors also appear to be involved in sedating and anti-excitatory effects of melatonergic drugs. This type of activity is mainly studied in relation to anti-convulsant role in which the role of melatonin is assessed on γ-aminobutyric acid (GABA) transmission.

The activity of test formulation may be through its action on GABA receptor complex that blocks GABA-mediated inhibition indicating that the drug is mediated by GABA receptors, not via 5-HT receptor inhibition and effect could be related to melatonergic action on the cholinergic system. Further, it is proposed that the drug may have alerting action. It is explained as 5-HT receptors are concentrated in frontal cortex, amygdala, hippocampus and cortico-limbic structures that are responsible in the regulation of mood and cognition.

Due to global awareness, attention has been directed towards the utilization of Ayurvedic plants in the prevention and management of many physical and mental disorders. In the Ayurvedic system of medicine, several drugs are known to influence the human behavior. But the scientific evidence is lacking. Due to the limitation of modern drugs, several plant based drugs have been advocated for the prevention and management of depression and associated behavioral changes. Ayurveda has listed a group of plants acting on brain function i.e. *Areca catechu* (L). *Bacopa monnieri* (L), *Celestrus paniculatus* (L). *Centella asiatica* (L), *Curcuma longa* (L), *Nardostachys jatamansi* (L), *Withania somnifera* (L), *Acorusm calamus*, *Argyreia speciosa*, *Clitoria ternatea*, *Convolulus pluricaulis*. *Dioscorea bublifera*. *Glycyrrhiza glabra*, *Jasminum sambac*, *Mucuna pruriens*, *Terminalia chebula*, *Tinosporu cordifolia*, *Valeriana jatamansi*, which are known to improve mental performance, regulation of behavior and sleep pattern. Out of these plants some of them i.e. *Areca catechu* (L), *Bacopa monnieri* (L), *Celestrus paniculatus* (L), *Centella asiatica* (L), *Curcuma longa* (L), *Withania somnifera* (L) are investigated for their cognitive function amelioration property. Taking the lead from ancient text we have investigated the anti-depressant property of plant based formulation containing the aqueous extract of *Nyctanhes arbor-tristis, Ocimum tenuiflorum* and *Hippophae salicifolia* on various biomarkers involved with different degrees of depression.

BRIEF SUMMARY OF THE INVENTION

An object of present invention is to propose a plant based anti-depressant drug for the management of mild to moderate depression.

Another object of this invention is to propose a plant based formulation having tricyclic or MAO inhibitory agent like activity.

Still another object of this invention is to propose a plant based formulation having potential to enhance melatonin concentration and improve the sleep pattern along with anxiety in depression cases.

Yet another object of this invention is to propose a plant based formulation which can regulate the altered neurotransmitter biochemistry in depression cases.

Further object of this invention is to propose a plant based formulation which can manage the mood affected behavior of depressive patients.

Still further object of this invention is to propose a plant based formulation for the management of emotional, social and cognitive functioning in depressive patients.

STATEMENT OF INVENTION

As per the present invention there is provided a novel plant based formulation showing therapeutic benefits in the management of mild to moderate depression through its potential therapeutic effects via acting on GABA receptors not via 5-HT receptor inhibition rather through its activity on melatonergic receptor in the cholinergic system. The drug may also have effects on 5-HT receptors accumulated in the frontal cortex, amygdala, hippocampus and cortico-limbic structures responsible for regulation of mood and cognition. It has been proposed that through circulatory neurotransmitters as well as neurotransmitters present in brain tissues, catecholamine and serotonin metabolism is impaired during mental depression.

Recent data suggested that 350 million people are affected from depression and out of 20 persons, 1 is having an episode of depression. As it is well established that the ultimate goal of anti-depressant treatment is the symptomatic and functional recovery helps a return to normal daily life functioning. Giving more importance to emotional, cognitive and social functioning in day to day life of depressive patients impaired functioning may have effect on a patient's life, therefore more alteration should be given on functioning when assessing the response of treatment of anti-depressant agent.

In the present study the pre-clinical safety and efficacy profile suggested that test formulation may exert its anti-depressant activity via its interaction with marker receptors i.e. melatonin and 5-HT The test formulation is beneficial in improving sleep and in desynchronizing the disturbed circadian rhythms making the test drug as a very useful, safe and effective anti-depressant agent. Thus the test formulation has potential to improve emotional, cognitive and social impaired behavior manifesting due to depressive behavior.

In fact depression is the leading cause of disease burden for women in both low as well as high income countries. Looking towards the global burden of depression which poses a substantial public health challenge both at social and economic levels as well as clinical levels, there are variety of evidence based therapeutic agents which can effectively combat this disease burden. Based on present study outcome it is proposed that treating depression following test formulation treatment is of clinical significance, affordable and also cost effective.

Based on the above approach of management of mild to moderate depression, under this invention there is provided a process for the preparation of present plant based formulation beneficial in the management of depression as claimed in claim 1. The test formulation comprising of aqueous extract of *Nyctanthes arbor-tristis* (Parijat—whole plant), *Ocimum tenuiflorum* (Van-Tulsi—whole plant) and *Hippophae salicifolia* (Seabuckthorn—Leaves & Fruits) in effective doses determined in pre-clinical studies as per GLP, GCP, ICH guidelines. The extraction of plant material was done at 70°–80° C. and maintaining the pH of solution between 4-6, separating the active compound chromatographically present in each plant extract by using TLC, HPLC and HPTLC supporting the molecular characterization of plant extract by utilizing IR & NMR The genetic bar coding of each plant was also done to confirm plant species, before starting the extraction process.

BRIEF DESCRIPTION OF THE DRAWINGS

FIG. 1 shows a process for providing a formulation according to one embodiment of the present invention.

DETAILED DESCRIPTION OF INVENTION

The aqueous extract of three medicinal plants found in the Tribal area of Madhya Pradesh i.e. *Nyctanthes arbor-tristis, Ocimum tenuiflorum* and *Hippophae salicifolia*, the extract was prepared using RO water and utilized for the development of present novel formulation. The Water utilized for extraction was decontaminated for any type of bacterial or abnormal growth by using reverse osmosis plant. After extraction the active molecules were identified and separated by HPLC, HPTLC and NMR methods. A mechanism based studies on each plant extract as well as combined formulation was carried out in various experimentally designed models. Both toxicity as well as the efficacy profile were studied. A dose dependent study was also conducted to determine the most active and safe dose of each plant extract. The pharmacological and biological activity of each plant extract selected to develop a new formulation for the management of depression of varying etiology was done through conducting mechanism based studies and the mode of action by assessing their effect on various targets involved with depression.

Under this procedure, the effect of test formulation was evaluated for its 5-HT and MAO inhibitory role as well as its activity as agonist of melatonin receptors in experimental studies. Standardization of biologically active material is another prerequisite for the determination of effective dose. Based on documents it has been observed that no clinical data is available to demonstrate the effects of this formulation on human behavior. In our preliminary clinical trial this formulation has shown beneficial effect in elevating the mood as well as improved sleep in depressed patients; as the test formulation has shown regulation of neurotransmitter system particular GABA & MAO activity along with its activity on rhythmic release in melatonin content among patients suffering from different degree of depression.

Extraction Procedure:

The shed dried raw material of *Nyctanthes arbor-tristis* (whole plant), *Ocimum tenuiflorum* (whole plant) and *Hippophae salicifolia* (Leaves & Fruits) were taken separately in corous form for extraction. The determination of presence of specific active molecules/active constituents as well as its quantification was done by using IR & NMR. The extraction was done at the temperature of 70°-80° C. and the pH of solution was maintained at 4-6. The following procedure was adopted to isolate the active compound, to evaluate and assess the biological activity of test formulation and to develop a new drug entity having a beneficial role in the management of mild to moderate depression. (FIG. 1).

Steps—Procedure

High through-put-screening of plant species chromatographic separation of active constituents is based on the following steps—

Identification of plant species→Chromatographic separation of active molecules→Structural elucidation of plant extracts→Quantification of molecules→Biotransformation-→Mechanism based studies→Toxico-kinetic study→Dose response curve→Behavioral correlates with bio-chemical parameters.

According to this invention there is provided a plant based formulation showing efficacy in the management of mild to moderate depression through its activity on neurotransmitter and biogenic pathways, behavior pattern and inducing sleep. The present test formulation comprising the following ingredients—

| Name of the plants | Part used |
|---|---|
| 1. *Nyctanthes arbortristis* | Whole plant |
| 2. *Ocimum tenuiflorum* | Whole plant |
| 3. *Hippophae salcifolia* | Leaves & Fruits |

Preferably the aforesaid plant extracts are present in the following dose range in the test formulation—

| Name of the plants | Dose |
|---|---|
| 1. *Nyctanthes arbortristis* | 225-450 mg/day |
| 2. *Ocimum tenuiflorum* | 250-550 mg/day |
| 3. *Hippophae salcifolia* | 200-450 mg/day |

The formulation may also comprise known additives such as minerals, vitamins, salt, filler (for capsulation or to prepare syrup) and binders, if required to present in trace amount.

Thus any known additive or supplement is added to prepare the final formulation required in trace amount. Reference is made here in capsule form. However, it would be apparent that the preparation may also be in the form of syrup/tablet.

Preferably but without implying any limitation the present preparation comprises the aqueous extract of following selected plants in the following effective doses.

Preferably the aforesaid plants are present in the following doses in the test formulation—

| Name of the plants | Dose |
|---|---|
| 1. *Nyctanthes arbortristis* | 325 mg/day |
| 2. *Ocimum tenuiflorum* | 350 mg/day |
| 3. *Hippophae salcifolia* | 275 mg/day |

Hypothesis:

Imbalance of GABA, glutamate and decreased amount of platelet MAO B and disturbance in melatonin metabolism are responsible for anxiety and depression. Several genes have been now recognized to influence anxiety and depression. Similarly regulation of various receptors like NMDA, AMPA, $MT_1$ and $MT_2$ including glutamatergic, serotonergic, monoaminergic receptors play a crucial role in the etiopathogenesis of depression.

Some medicinal plants have shown significant effect in the modulation of various neurotransmitter systems including GABA and glutamate levels. Similarly some of plant extracts have shown significant effect in enhancement of melatonin which regulates the sleep pattern. Regulation of sleep patterns which is under the control of clock gene may serve as a useful target for management of depression.

The plants selected in the study contains various molecules have shown a significant role in management of depression by maintaining GABA-Glutamate homeostasis.

Further, regulation of platetet monoamine-oxidase activity also play important role in the management of depression and as well as regulation of sleep pattern.

In present invention combined effect of 3 plants containing specific bio-molecules acts on above receptors has been evaluated.

In order to prove above hypothesis, a novel process has been developed by using various inventive steps to propose a new drug in the management of mild to moderate depression.

1. *Nyctanthes arbor-tristis* (Night-flowering Jasmine) is a species of *Nyctanthes*, belongs to family Oleaceae found all over the country. The major chemical constituents present in various parts of the plant is the leaves contain β-sitosterol, flavanol glycosides, oleanolic acid, ascorbic acid, lupeol, glycosides, etc. The flowers mainly contain essential oils, carotenoids, glycosides. The seeds contain linoleic, palmitic and a water soluble polysaccharide. The bark contains glycosides and alkaloids. In stems the major chemical constituents found are glycoside, β-sitosterol. However, the active constituents found in leaves of the plant have activity like anti-inflammatory, hepatoprotective, immunopotentiating and antioxidant. Flowers mainly have activity like anti-inflammatory, anti-oxidant and sedative. On the whole the pharmacological activity of this plant is sedative, anti-inflammatory, anti-oxidant and immunomodulatory.

2. *Hippophae salicifolia* (Seabuckthorn)—This is high altitude plant belongs to family Elaeagnaceae. Fruits and leaves have shown medicinal property. *Hippophae salicifolia* is a rich source of flavonoids, vitamins, proteins, amino acids, folic acid, phytosterol, alpha-tocopherol and phenolic compounds. It has shown anti-oxidant, immuno-modulatory, anti-inflammatory and homocysteine lowering effects and uplifts the mental function.

3. *Ocimum tenuiflorum* (Van Tulsi), This plant belongs to family Lamiaceae, it has wild growth and available throughout the Eastern World Tropics. Some of the main chemical constituents of this plant is eugenol, oleanolic acid, ursolic acid, rosmarinic acid, etc. The main pharmacological activity is COX-2 inhibitor, analgesic effect due to high concentration of eugenol, anti-oxidant, repairs cell damage due to exposure to radiation, anti-hyperlipidemic and cardioprotective effects, promotes immune system function.

Rationale for Selection of Plants:

Based on various pre-clinical and clinical studies it has been postulated that the active molecules present in three plants regulates the GABA-Glutamate balance, inhibits the MAO activity and regulates the Melatonin secretion. Thus the combined formulation is beneficial in the management of depression.

EXAMPLE

Example-1

When the aqueous extract *Nyctanthes arbor-tristis* (75 mg/kg), *Ocimum tenuiflorum* (75 mg/kg) and *Hippophae salicifolia* (50 mg/kg) was administered orally to animals of sleep deprivation stress model exhibited its activity as 5-HT antagonist as well as melatonin agonist effects suggesting improved sleep pattern as well as its anti-depressant potentials. The drug is having $5-HT_{2c}$ receptor antagonist activity as it inhibits serotonin re-uptake by acting on several neuroplasticity associated molecules in the associated brain region. 5-HT antagonism will predominate on melatonergic action.

Example-2

The aqueous extract of *Ocimum tenuiflorum* in the dose of 125 mg/kg and *Hippophae salicifolia* in the dose of 125 mg/kg mixed and given to experimentally designed sleep deprived rats a significant reduction in glutamate content was noticed along with increase in GABA synthesis, suggesting the improved brain function impairment in terms of anti-depressant activity of test drug. Overall the neuronal plasticity was enhanced. The test formulation acted as $MT_1$ and $MT_2$ agonist and maintained the hippocampal volume, Example-3

After determination of safety and efficacy of test formulation in pre-clinical studies the test formulation was utilized for human consumption. When the aqueous extract of *Nyctanthes arbor-tristis* in the dose of 425 mg/day and *Ocimum tenuiflorum* in the dose of 450 mg/day was mixed and given to selected cases of mild to moderate depression, improvement in loss of interest in various activities, loss of self esteem, loss of energy and depressed mood was noticed through its activity on neurotransmitter biochemistry.

Example-4

When the aqueous extract of *Nyctanthes arbor-tristis* in the dose of 375 mg/day and *Hippophae salicifolia* in the dose of 400 mg/day was given to selected depression cases a very good response in improving the functional impairment was noticed among depressive patients. The psychomotor co-ordination/retardation of depressed patients improved and a better cognitive function was recorded in selected depression cases.

Example-5

When the aqueous extract of *Nyctanthes arbor-tristis* in the dose of 450 mg/day and *Ocimum tenuiflorum* in the dose of 425 mg/day orally administered to patients with depressive behavior improvement in fatigue (energy) and general body immunity was noticed. The early fatigue time enhanced significantly after treatment with test formulation determined through Electronic Fatigue Time Apparatus.

Example-6

The Aqueous extract of *Ocimum tenuiflorum* in the dose of 375 mg/day and *Hippophae salicifolia* in the dose of 450 mg/day given in combined form to diagnosed depressive patients the sleep duration enhanced, sleep/wake cycle pattern suggested the improvement in sleep and early morning wake including quality of every day performance of the patients.

Example-7

When the aqueous extract of *Nyctanthes arbor-tristis* in the dose of 375 mg/day, *Ocimum tenuiflorum* in the dose of 325 mg/day and *Hippophae salicifolia* in the dose of 225 mg/day given in combined form to depression cases a complete and sustained recovery from depression, psychosocial impairments was noticed. The anti-depressant activity of test drug is through the prevention of breakdown like MAO inhibitor or reduction in re-uptake like tricyclic agent.

Example-8

When the aqueous extract of *Nyctanthes arbor-tristis* in the dose of 400 mg/day, *Hippophae salicifolia* in the dose of 375 mg/day and *Ocimum tenuulorum* in the dose of 150 mg/day orally given in combined form to depression cases a significant decrease in depression scores were noticed when evaluated on Beck Depression Inventory Scale.

Example-9

When the aqueous extract of *Nyctanthes arbor-tristis* in the dose of 425 mg/day, *Hippophae salicifolia* in the dose of 350 mg/day and *Ocimum tenuiflorum* in the dose of 175 mg/day given to selected depression patients the Hamilton Depression Rating Scale analysis showed remarkable decrease in depression scores along with reduction in anxiety scores also.

Example-10

When the aqueous extract of *Nyctanthes arbor-tristis* in the dose of 325 mg/day, *Ocimum tenuiflorum* in the dose of 350 mg/day and *Hippophae salicifolia* in the dose of 275 mg/day given to mild to moderate depression patients most effective results were obtained. The novel test formulation is an agonist of $MT_1$ and $MT_2$ melatonin receptors and an antagonist of $5\text{-}HT_{2c}$ receptors. Its anti-depressant activity is proven through its interaction with both type of receptors. The psychosocial impairment increases the severity of depressive symptoms, greatly improved social functioning, improved personal and professional functioning among patients with depression, resulting in improvement in routine quality of physical and mental work performance.

The test formulation revealed disease remission, improved functional impairment scores related to emotional, cognitive and social factors. An improvement in loss of interest, decreased self esteem, loss of energy, depressed mood was noticed which corrects the patients ability to maintain relationship under influence of test formulation treatment.

Regulation of Biogenic Amines Following Combined Formulation Treatment:

The study is divided into four groups, 10 rats of Charles foster strain were kept in each study group.

Group-I:

In control group 10 rats were selected and kept on normal saline for 7 days. On $7^{th}$ days the animals were sacrificed and various biogenic amines like 5-HT GABA & glutamate, melatonin and MAO were estimated. After dissection of rat's brain the biogenic amines were estimated in thalamus, hypothalamus and cortex.

Group-II:

In this group sleep deprivation stress for 7 days was given to all the 10 rats. After 7 days the rat's brain were dissected and thalamus, hypo-thalamus and cortex were separated for the measurement of brain biogenic amines.

Group-III:

In this group the sleep deprivation stress was introduced along with the hydro-alcoholic extract of three plants *Nyctanthes arbor-tristis, Ocimum* tenuiflorum and *Hippophae salicifolia*. The drug *Nyctanthes arbor-tristis* (100 mg/kg bw./day), *Ocimum tenuiflorum* (50 mg/kg bw./day), *Hippophae salicifolia* (50 mg/kg bw./day) was given in combined form to all the 10 rats along with sleep deprivation stress. On $7^{th}$ day (after two hours of administration of test drug) different parts of the rat's brain were dissected and 5-HT, melatonin GABA. glutamate and histamine were measured.

Group-IV:

The modern drug "'Librium" was given in the dose of 2 mg/kg/day for 7 days along with sleep deprivation stress. On $7^{th}$ days the animals were sacrifice and brain biogenic amines were estimated in different parts of rat's brain.

The value obtained were compared with each other group (Normal vs sleep deprivation stress and sleep deprivation stress vs sleep deprivation stress+test formulation and sleep deprivation stress vs modern drug treatment group. Apart from initial at 7 day before sacrificing the animals circulating biogenic amines were also measured in all the three groups.

Observation and Result:

As per the object of the present experimental study the effect of test formulation containing the hydro-alcoholic extract of three plants *arbor-tristis, Ocimum tenuiflorum* and *Hippophae salicifolia* in effective doses was orally induced to animals following sleep deprivation stress. The beneficial role is evaluated on various brain biogenic amines.

It is observed that 7 days sleep deprivation stress exerted marked alteration on brain biogenic amines i.e. 5-HT, melatonin, GABA, glutamate and also a biogenic amines like GABA, glutamate, 5-HT, MAO, histamine and histaminase levels, 5-HT level increased markedly following sleep deprivation in all the three parts of brain. The increase in the level is significantly less in test formulation treated group following sleep deprivation stress (Table 1).

Melatonin and GABA levels were significantly decreased following stress in comparison to normal control group. The test formulation revealed its beneficial role in controlling the decline of levels as decrease is significantly less in GABA content following stress (Table 2-3).

The experimental rats following sleep deprivation stress showed a significant rise in glutamate content in the different parts of the brain. The 7 days treatment with test drug along with stress the increase in the glutamate content is quite less than the negative control group (Table 4).

The circulating brain biogenic amines GABA, glutamate, 5-HT, histamine and histaminase significantly increased following sleep deprivation stress where as MAO levels were decreased under stress. All these altered levels of circulating biogenic amines regulated under Ayurvedic test drug therapy. Decrease in MAO levels were significantly less in treated groups than only sleep deprivation stress groups of animals (Table5).

It is observed that the modern drug Librium exerted better results on the neurochemical parameters but keeping the adverse reaction and restricted application of modern synthetic chemicals used for inducing sleep, the present Ayurvedic test formulation may be a better choice of drug in the regulation of sleep patterns.

TABLE 1

Beneficial role of test formulation on 5-HT level in experimental sleep deprivation stress model.

| Groups | No. of Animals | 5-HT (µg/gm in wet tissue) | | |
| --- | --- | --- | --- | --- |
| | | Hypothalamus | Thalamus | Cortex |
| Normal control * | 10 | 1.685 ± 0.162 | 1.345 ± 0.295 | 0.852 ± 0.238 |
| Sleep deprivation ** Stress | 10 | 2.876 ± 0.356 | 1.918 ± 0.306 | 1.476 ± 0.238 |
| Sleep deprivation streess + test formulation *** | 10 | 2.196 ± 0.446 | 1.530 ± 0.285 | 1.145 ± 0.372 |

TABLE 1-continued

| | | | | |
|---|---|---|---|---|
| Sleep deprivation stress + Librium (2 mg/kg) **** | 10 | 1.942 ± 0.315 | 1.460 ± 0.218 | 1.093 ± 0.118 |

Comparison
| | | | |
|---|---|---|---|
| * vs ** | $P < 0.001$ | $P < 0.001$ | $P < 0.001$ |
| ** vs *** | $P < 0.01$ | $P < 0.02$ | $P < 0.01$ |
| *** vs **** | $P < 0.05$ | $P < 0.05$ | $P < 0.05$ |

TABLE 2

Beneficial role of test formulation on melatonin level in experimental sleep deprivation stress model.

| | | Melatonin (μg/gm in wet tissue) | | |
|---|---|---|---|---|
| Groups | No. of Animals | Hypothalamus | Thalamus | Cortex |
| Normal control * | 10 | 11.67 ± 3.02 | 7.99 ± 3.46 | 9.86 ± 2.08 |
| Sleep deprivation ** Stress | 10 | 5.91 ± 1.34 | 3.98 ± 2.01 | 4.73 ± 2.32 |
| Sleep deprivation stress + test formulation *** | 10 | 9.33 ± 3.01 | 5.31 ± 2.38 | 6.25 ± 2.95 |
| Sleep deprivation stress + Librium (2 mg/kg) **** | 10 | 7.80 ± 1.02 | 5.95 ± 1.85 | 7.01 ± 1.46 |

Comparison
| | | | |
|---|---|---|---|
| * vs ** | $P < 0.001$ | $P < 0.001$ | $P < 0.001$ |
| ** vs *** | $P < 0.01$ | $P < 0.02$ | $P < 0.01$ |
| *** vs **** | $P < 0.01$ | $P < 0.05$ | $P < 0.01$ |

TABLE 3

Effect of test formulation on GABA content in the brain following experimental sleep deprivation stress.

| | | GABA (μmol/gm in wet tissue) | | |
|---|---|---|---|---|
| Groups | No. of Animals | Hypothalamus | Thalamus | Cortex |
| Normal control * | 10 | 3.48 ± 0.50 | 2.17 ± 0.39 | 1.72 ± 0.42 |
| Sleep deprivation ** Stress | 10 | 6.84 ± 1.39 | 5.04 ± 1.12 | 4.32 ± 0.77 |
| Sleep deprivation stress + test formulation *** | 10 | 4.80 ± 1.22 | 3.75 ± 0.82 | 2.94 ± 0.82 |
| Sleep deprivation stress + Librium (2 mg/kg) **** | 10 | 4.68 ± 1.02 | 3.91 ± 0.58 | 2.62 ± 0.59 |

Comparison
| | | | |
|---|---|---|---|
| * vs ** | $P < 0.001$ | $P < 0.001$ | $P < 0.001$ |
| ** vs *** | $P < 0.01$ | $P < 0.02$ | $P < 0.02$ |
| *** vs **** | $P < 0.05$ | $P < 0.05$ | $P < 0.05$ |

TABLE 4

Effect of test formulation on glutamate level following experimental sleep deprivation stress.

| | | Glutamate (μmol/gm in wet tissue) | | |
|---|---|---|---|---|
| Groups | No. of Animals | Hypothalamus | Thalamus | Cortex |
| Normal control * | 10 | 11.02 ± 2.98 | 13.06 ± 3.24 | 14.91 ± 2.64 |
| Sleep deprivation ** Stress | 10 | 16.95 ± 2.56 | 18.04 ± 3.11 | 17.22 ± 4.01 |
| Sleep deprivation stress + test formulation *** | 10 | 13.88 ± 2.80 | 13.82 ± 2.75 | 14.80 ± 2.73 |
| Sleep deprivation stress + Librium (2 mg/kg) **** | 10 | 12.66 ± 3.06 | 11.64 ± 3.01 | 13.97 ± 2.11 |

Comparison
| | | | |
|---|---|---|---|
| * vs ** | $P < 0.001$ | $P < 0.001$ | $P < 0.001$ |
| ** vs *** | $P < 0.01$ | $P < 0.02$ | $P < 0.01$ |
| *** vs **** | $P < 0.05$ | $P < 0.05$ | $P < 0.05$ |

TABLE 5

Beneficial role of test formulation on circulating biogenic amines following experimental sleep deprivation stress.

| Groups | GABA (μmol/ml) | Glutamate (μmol/ml) | 5-HT (μg/ml) | MAO (nmol/m/hrs.) | Histamine (μg/ml) | Histaminase (μg/ml) |
|---|---|---|---|---|---|---|
| Normal Control * (N = 10) | 0.91 ± 0.22 | 0.79 ± 0.19 | 0.14 ± 0.10 | 3.90 ± 0.65 | 0.19 ± 0.05 | 30.20 ± 4.32 |
| Sleep deprivation ** Stress (N = 10) | 1.68 ± 0.19 | 1.26 ± 0.12 | 0.58 ± 0.20 | 7.04 ± 1.22 | 0.51 ± 0.15 | 49.65 ± 5.30 |
| Sleep deprivation stress + test formulation *** (N = 10) | 1.22 ± 0.20 | 0.95 ± 0.15 | 0.30 ± 0.12 | 5.28 ± 1.30 | 0.32 ± 0.11 | 39.70 ± 3.38 |
| Sleep deprivation stress + Librium (2 mg/kg) **** (N = 10) | 1.02 ± 0.18 | 1.11 ± 0.10 | 0.26 ± 0.15 | 4.72 ± 0.89 | 0.45 ± 0.10 | 35.46 ± 4.95 |

Comparison
* vs **    $P < 0.001$   $P < 0.001$   $P < 0.001$   $P < 0.001$   $P < 0.001$   $P < 0.001$
 vs *  $P < 0.01$    $P < 0.01$    $P < 0.01$    $P < 0.01$    $P < 0.02$    $P < 0.001$
* vs ** $P > 0.05$   $P > 0.05$    $P > 0.05$    $P > 0.05$    $P > 0.05$    $P > 0.05$ Clinical Study Material and Methods In the present study 99 cases between the age group of 20 to 60 years presenting the symptoms of mild to moderate depression were selected for clinical trial of test formulation containing extract of *Nyctanthes arbor-tristis*, *Ocimum tenuiflorum* and *Hippophae salicifolia*. The subjects were advised to take test formulation twice in a day in two divided doses (475 mg morning and 475 mg in the evening). The level of mood was measured by Major Depression Inventory (MDI) developed by Olsen L R et al (2003), the fatigue and psychomotor performance was measured by Mental Fatigue Apparatus and Rotary Pursuit Task. These tests and test battery are recommended by Gupta and Dubey (1994) for the scientific and objective assessment in the area of drug development. The behavioral pattern was repeatedly assessed at the continuous interval of one month for six months.

In control series (Sertraline treated) all the investigations were repeated and compared with the treated group.

Results

It is observed that specific clinical features such as lack of interest, poor sleep, poor appetite, weight loss, and psychomotor retardation showed considerable improvement after six months of continuous administration of test formulation. In the treated group significant improvement in clinical symptomatology, after six months of treatment was noticed, whereas the conventionally treated group did not exert such improvement in this series (Table-1).

TABLE 1

Improvement in clinical symptomatology (in percent) following test formulation treatment.

| | Treated with Sertraline | | Test formulation treated | |
|---|---|---|---|---|
| Clinical symptomatology | Initial | After 6 months | Initial | After 6 months |
| Lack of interest | 97.82 | 92.20* | 98.42 | 75.51° |
| Poor concentration | 88.41 | 86.02* | 92.73 | 82.90° |
| Pessimistic thinking | 96.27 | 95.86* | 95.90 | 87.32° |
| Early fatiguability | 98.01 | 91.12* | 97.45 | 78.26° |
| Poor sleep | 98.04 | 79.41* | 96.34 | 74.35° |
| Poor appetite | 58.89 | 50.03* | 61.33 | 33.78° |
| Weight loss | 42.01 | 40.32* | 43.81 | 17.35° |
| Psychomotor retardation | 74.66 | 78.09* | 79.11 | 57.35° |

*No improvement in percent;
°Improvement in percent

The alpha brain wave which indicates the relaxed state of mind also showed significant improvement in the treated group. The initial value of alpha wave significantly increased after six months treatment. However, the control group did not show any change in the alpha pattern (Table 2).

TABLE 2

Effect of test formulation on alpha brain wave among minor depressive cases

| | | Alpha Brain Wave (Hz) | | | | Comparison |
|---|---|---|---|---|---|---|
| Groups | Sample size | Initial | After 2 months | After 4 month | After 6 months | Initial Vs After 6 months |
| Sertraline treated | 41 | 6.18 ± 2.03 | 6.31 ± 2.41 | 5.93 ± 2.18 | 5.76 ± 1.93 | $p > 0.05$ |
| Test formulation treated | 58 | 5.92 ± 2.47 | 7.56 ± 2.91 | 9.15 ± 3.23 | 10.38 ± 3.19 | $P < 0.05$ |

The mental fatigue level also showed considerable improvement after six months of treatment in comparison to control group. The initial value of mental fatigue level significantly increased after six months in the treated group (Table 3).

TABLE 3

Effect of test formulation on mental fatigue level among minor depressive cases

| Groups | Sample size | Mental fatigue level (Hz) | | | | Comparison Initial Vs |
|---|---|---|---|---|---|---|
| | | Initial | After 2 months | After 4 months | After 6 months | After 6 months |
| Sertraline treated | 41 | 18.22 ± 3.17 | 19.68 ± 4.02 | 19.02 ± 3.72 | 18.45 ± 2.11 | P > 0.05 |
| Test formulation treated | 58 | 17.86 ± 3.16 | 21.24 ± 2.90 | 23.10 ± 3.62 | 24.98 ± 3.87 | P > 0.05 |

The rotatory-pursuit task which measures psychomotor performance showed significant improvement after six months of treatment of test formulation in minor depressive cases. The task performance considerably improved in the treated group as errors reduced significantly after six months of therapy in comparison to the control group (Table 4).

TABLE 4

Effect of test formulation on psychomotor coordination among minor depressive cases

| Groups | Sample size | Rotatory pursuit task (Hz) | | | | Comparison Initial Vs |
|---|---|---|---|---|---|---|
| | | Initial | After 2 months | After 4 months | After 6 months | After 6 months |
| Sertraline treated | 41 | 28.39 ± 3.74 | 28.03 ± 3.58 | 27.47 ± 2.14 | 26.52 ± 3.46 | P > 0.05 |
| Test formulation treated | 58 | 30.13 ± 4.57 | 28.42 ± 4.73 | 25.98 ± 5.13 | 24.78 ± 5.02 | P > 0.05 |

TABLE 5

Changes in anxiety level and mental fatigue time following oral administration of test formulation in depressive disorder cases.

| Treatment groups | Sample size | Anxiety level (score) | | Comparison (initial vs after 6 months) | Mental fatigue (Time) | | Comparison (initial vs after 6 months) |
|---|---|---|---|---|---|---|---|
| | | Initial | After 6 months | | Initial | After 6 month | |
| Sertraline treated | 41 | 56.5 ± 4.78 | 58.5 ± 3.35 | <0.05 | 94.5 ± 12.85 | 90.3 ± 10.78 | >0.05 |
| Test formulation treated | 58 | 61.40 ± 3.11 | 54.82 ± 3.79 | <0.05 | 86.6 ± 14.87 | 70.77 ± 12.85 | <0.05 |

TABLE 6

Change in attention and alpha frequency after oral administration of test formulation in depression patients.

| Clinical groups | Attention span (Score) | | Comparison (Initial vs after 6 months) | Alpha frequency (Hz) | | Comparison (initial vs after 6 months) |
|---|---|---|---|---|---|---|
| | Initial | After 6 months | | Initial | After 6 months | |
| Sertraline treated (N = 41) | 10.49 ± 2.78 | 9.32 ± 1.64 | >0.05 | 6.42 ± 1.08 | 7.92 ± 0.73 | >0.05 |
| Test formulation treated (N = 58) | 8.73 ± 2.45 | 12.68 ± 2.01 | <0.05 | 5.98 ± 1.22 | 8.12 ± 2.06 | <0.05 |

TABLE 7

Effect of test formulation on GABA and glutamate levels in depression cases.

| Clinical groups | GABA (μmol/ml) | | Comparison (Initial vs after 6 months) | Glutamate (μmol/ml) | | Comparison (initial vs after 6 months) |
|---|---|---|---|---|---|---|
| | Initial | After 6 months | | Initial | After 6 months | |
| Sertraline treated (N = 41) | 1.070 ± 0.385 | 1.410 ± 0.475 | >0.05 | 0.419 ± 0.094 | 0.385 ± 0.092 | >0.05 |
| Test formulation treated (N = 58) | 1.64 ± 0.421 | 1.02 ± 0.211 | <0.05 | 0.502 ± 0.101 | 0.386 ± 0.099 | <0.05 |

TABLE 8

Changes in platelet MAO activity following oral adminstration of test formulation in depressive disorder cases.

| Clinical groups | Platelet MAO (nmol/ml/hr) | | Comparison (Initial vs after 6 months) | Glutamate (nmol/mg/hr) | | Comparison (initial vs after 6 months) |
|---|---|---|---|---|---|---|
| | Initial | After 6 months | | Initial | After 6 months | |
| Sertraline treated (N = 41) | 5.04 ± 1.62 | 5.98 ± 1.35 | >0.05 | 3.14 ± 0.08 | 4.23 ± 1.01 | >0.05 |
| Test formulation treated (N = 58) | 6.11 ± 2.04 | 4.21 ± 0.77 | <0.05 | 4.10 ± 0.85 | 2.87 ± 0.31 | <0.05 |

TABLE 9

Changes in epinephrine and norepinephrine level under influence of test formulation in depressive cases.

| Clinical groups | | Epinephrine ng/ml | | Comparison (initial vs after 6 months) | Norepinephrine ng/nl | | Comparison (initial vs after 6 months) |
|---|---|---|---|---|---|---|---|
| | | Initial | After 6 months | | Initial | After 6 months | |
| Depression | C (N = 41) | 5.32 ± 1.308 | 6.42 ± 1.928 | >0.05 | 8.5 ± 1.83 | 9.82 ± 1.78 | >0.05 |
| | T (N = 58) | 6.20 ± 1.378 | 4.40 ± 1.038 | <0.05 | 7.5 ± 2.85 | 6.20 ± 1.132 | >0.05 |

TABLE 10

Decrease in interleukin-1 β concentration following test formulation treatment among mild to moderate depressive patients.

| Groups | Sample size | IL-1 β (µg/ml) | | | | Comparison Initial Vs |
|---|---|---|---|---|---|---|
| | | Initial | After 2 months | After 4 months | After 6 months | |
| Sertraline treated | 41 | 2.098 ± 0.624 | 1.886 ± 0.312 | 1.923 ± 0.228 | 1.790 ± 0.312 | P > 0.05 |
| Test formulation treated | 58 | 2.194 ± 0.921 | 1.773 ± 0.624 | 1.462 ± 0.558 | 1.398 ± 0.486 | P > 0.05 |

TABLE 11

Effect of test formulation on TNF-α among mild to moderate depressive patients.

| Groups | Sample size | TNF-1 α (ng/mL) | | | | Comparison Initial Vs |
|---|---|---|---|---|---|---|
| | | Initial | After 2 months | After 4 months | After 6 months | |
| Sertraline treated | 41 | 4.82 ± 1.06 | 3.71 ± 1.22 | 3.85 ± 1.12 | 4.14 ± 1.06 | P > 0.05 |
| Test formulation treated | 58 | 5.13 ± 1.06 | 4.63 ± 1.02 | 4.19 ± 0.98 | 3.58 ± 0.88 | P < 0.01 |

TABLE 12

Effect of test formulation on TNF-α among mild to moderate depressive patients.

| Groups | Sample size | DHA (g/100 g of total fatty acid) | | | | Comparison Initial Vs |
|---|---|---|---|---|---|---|
| | | Initial | After 2 months | After 4 months | After 6 months | |
| Sertraline treated | 41 | 1.096 ± 0.246 | 1.082 ± 0.193 | 1.920 ± 0.214 | 1.980 ± 0.318 | P > 0.05 |
| Test formulation treated | 58 | 1.047 ± 0.106 | 1.284 ± 0.293 | 1.886 ± 0.421 | 2.011 ± 0.389 | P < 0.01 |

TABLE 13

Decrease in muscle action potential following test formulation treatment in depression cases

| Groups | Sample size | Occipito frontalis muscle action potential | | | | Comparison Initial Vs |
|---|---|---|---|---|---|---|
| | | Initial | After 2 months | After 4 months | After 6 months | |
| Sertraline treated | 41 | 4.378 ± 17.23 | 41.75 ± 15.25 | 42.82 ± 11.64 | 40.86 ± 16.22 | P > 0.02 |
| Test formulation treated | 58 | 57.13 ± 21.45 | 45.87 ± 15.90 | 37.22 ± 20.42 | 33.49 ± 13.25 | P < 0.001 |

TABLE 14

Delta activation following test formulation treatment in depression cased

| Groups | Sample size | Delta Wave (Hz) | | | | Comparison Initial Vs |
|---|---|---|---|---|---|---|
| | | Initial | After 2 months | After 4 months | After 6 months | |
| Sertraline treated | 41 | 0.68 ± 0.09 | 0.94 ± 0.12 | 1.06 ± 0.11 | 1.02 ± 0.10 | P > 0.05 |
| Test formulation treated | 58 | 0.71 ± 0.13 | 1.22 ± 0.09 | 1.45 ± 0.13 | 1.64 ± 0.16 | P < 0.001 |

TABLE 15

Increase in Neuro-peptide-γ content following test formulation treatment in depressed patients

| Groups | Sample size | Neuro-peptide-γ (pg/ml) | | | | Comparison Initial Vs After 6 months |
|---|---|---|---|---|---|---|
| | | Initial | After 2 months | After 4 months | After 6 months | |
| Sertraline treated | 24 | 129.68 ± 17.22 | 148.90 ± 30.25 | 151.89 ± 29.87 | 156.04 ± 13.77 | P < 0.05 |
| Test formulation treated | 36 | 133.80 ± 14.02 | 168.92 ± 27.25 | 192.45 ± 26.87 | 228.93 ± 38.04 | P < 0.01 |

TABLE 16

Table shows improvement in sleep pattern following test formulation treatment in depressive patients

| Groups | No. of cases | Before treatment | | | After 6 months treatment | | |
|---|---|---|---|---|---|---|---|
| | | Sleep period (min) | Total Sleep (min) | Sleep Latency (min) | Sleep period (min) | Total Sleep (min) | Sleep Latency (min) |
| Sertraline treated | 60 | 445.90 ± 20.11 | 234.98 ± 35.80 | 13.62 ± 2.41 | 438.35 ± 30.78 | 201.94 ± 39.73 | 14.98 ± 3.17 |
| Test formulation treated | 82 | 438.73 ± 31.64 | 211.06 ± 23.73 | 14.04 ± 2.73 | 439.74 ± 25.73 | 314.97 ± 36.82 | 11.79 ± 2.45 |

TABLE 17

Effect of test formulation on sleep pattern recorded in terms of different stages among depressive patients

| Groups | No. of cases | Before treatment | | | | After 6 months treatment | | | |
|---|---|---|---|---|---|---|---|---|---|
| | | Stage-I (Time in min) | Stage-II (Time in min) | Stage-III (Time in min) | Stage-IV (Time in min) | Stage-I (Time in min) | Stage-II (Time in min) | Stage-III (Time in min) | Stage-IV (Time in min) |
| Sertraline treated | 60 | 179.32 ± 21.74 | 45.82 ± 6.11 | 18.22 ± 3.97 | Could not reach | 162.98 ± 42.74 | 46.22 ± 9.31 | 15.82 ± 4.73 | Could not reach |
| Test formulation treated | 82 | 174.93 ± 14.73 | 48.20 ± 7.11 | 20.68 ± 6.02 | Could not reach | 178.93 ± 21.73 | 34.79 ± 5.11 | 16.22 ± 3.97 | Could not reach |

The neuro-chemical assessment exhibited modulation of altered neuro-transmitters and biogenic amines after treatment with test formulation in selected depression cases (Table 5-9). The inflammatory cytokines 1L-1β and TNF-α decreased significantly in test formulation treated group indicating beneficial role of test formulation in reducing the severity as well as frequency of depressive episodes among mild to moderate depressive patients (Table-10 & 11). There is an increase in DHA content after oral administration of test formulation for 6 months (Table-12). Table-13 shows a marked decrease in occipito frontalis muscle action potentials following test formulation treatment indicating a decrease in anxiety and tension among depressed persons. Similarly the test formulation also exerted delta activation after treatment in depressed patients suggesting improvement in the sleep pattern of the patients (Table-14). Neuro-peptide-γ is the 36-amino acid which affects anxiety, stress, pain, circadian rhythm and also associated various psychiatric disorders particularly depression of varying degree. The test formulation exerted significant increase in NP-γ content in the brain suggesting improvement in anxiety, stress and depressive behavior of the depression patients (Table-15). The effect of test formulation on sleep pattern measured by recording on polysomnographic studies indicated improvement in sleep period, total sleep, sleep latency and various stages of sleep. Though none of the cases could achieve the stage four. The results obtained in the test formulation treatment group were compared with the conventional drug treated group and exerted significant difference when the conventional treated group was compared with the test formulation treated group (Table-16-17). The drug was found safe and effective after 6 months of continuous oral administration to depressed patients. From the results, it is evident that the oral administration of the test formulation is an effective and well tolerated drug for the management of mild to moderate depression.

The invention claimed is:

1. An anti-depressant tablet or capsule consisting essentially of therapeutically effective amounts of *Nyctanthes arbor-tristis* extract, *Ocimum tenuiflorum* extract, and *Hippophae salicifolia* extract.

2. The tablet or capsule of claim 1, wherein said *Nyctanthes arbor-tristis* is from the whole plant, the *Ocimum tenuiflorum* is from the whole plant and the *Hippophae salicifolia* is from the fruit and leaf.

3. The tablet or capsule of claim 1, wherein the amount of each of the components are:
   325 mg of *Nyctanthes arbor-tristis*;
   350 mg of *Ocimum tenuiflorum*; and
   275 mg of *Hippophae salicifolia*.

4. A process for making the tablet or capsule of claim 1, consisting essentially of:
   a) grinding a portion of *Nyctanthes arbor-tristis, Ocimum tenuiflorum* and *Hippophae salicifolia* to yield ground herbal matter;
   b) subjecting the ground herbal matter to a step of extraction using water to yield an extract;
   c) filtering the extract to provide a filtered product;
   d) subjecting the filtered product to a step of distillation under vacuum; and
   e) grinding and sieving the filtered product to then be tableted or capsulated to produce the tablet or capsule.

5. The process of claim 4, wherein the temperature at time of the extraction is 70°–80° C. and the extraction process lasts for a period of 3-4 hours.

6. The process of claim 4, wherein the distillation is performed at 65° C.

7. A method for treating depression in a human in need thereof consisting essentially of administering to said human in need thereof a therapeutically effective amount of the tablet or capsule of claim 1 to promote sleep pattern and improve wake-cycle and depression symptoms in the human in need thereof.

8. A method for treating depression in a human in need thereof consisting essentially of administering to said human in need thereof therapeutically effective amounts of the tablet or capsule of claim 1 to ameliorate symptoms of depression in the human in need thereof.

9. The method of claim 8, wherein said administering of the tablet or capsule improves brain functional impairment, maintains hippocampal volume, and/or enhances neuronal plasticity in the human in need thereof.

10. The method of claim 8, wherein the administering of the tablet or capsule improves sleep quality in the human in need thereof.

11. A method of treating depression in a human in need thereof consisting essentially of administering to said human in need thereof therapeutically effective amounts of the tablet or capsule of claim 1 to ameliorate symptoms of depression in the human in need thereof.

12. The method of claim 11, wherein the administering reduces anxiety and/or phobic reactions in the human in need thereof.

13. The method of claim 11, wherein the administering improvises diffusion and hallucinations in the human in need thereof.

14. The method of claim 11, wherein the administering enhances immunity and/or improves fatigue in the human in need thereof.

* * * * *